(12) United States Patent
Mitchiner et al.

(10) Patent No.: US 6,663,555 B2
(45) Date of Patent: *Dec. 16, 2003

(54) PERMANENT MAGNET KEEPER-SHIELD ASSEMBLY

(75) Inventors: Robert Mitchiner, Longmont, CO (US); Thomas B. Kent, Boulder, CO (US); Caryn Peterson, Encinitas, CA (US); Scott Raymond Rudge, Boulder, CO (US)

(73) Assignee: Ferx Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/087,442

(22) Filed: Mar. 1, 2002

(65) Prior Publication Data

US 2002/0188165 A1 Dec. 12, 2002

Related U.S. Application Data

(63) Continuation of application No. 09/538,952, filed on Mar. 31, 2000, now Pat. No. 6,488,615.

(51) Int. Cl.[7] ................................................. A61N 2/00
(52) U.S. Cl. ........................................................ 600/9
(58) Field of Search .......................................... 600/9–15

(56) References Cited

U.S. PATENT DOCUMENTS

| | | |
|---|---|---|
| 5,412,365 A | 5/1995 | Abele et al. |
| 5,549,915 A | 8/1996 | Volkonsky et al. |
| 5,651,989 A | 7/1997 | Volkonsky et al. .......... 424/490 |
| 5,705,195 A | 1/1998 | Volkonsky et al. .......... 424/490 |
| 5,900,793 A | 5/1999 | Katznelson et al. |
| 6,200,547 B1 | 3/2001 | Volkonsky et al. |
| 6,488,615 B1 * | 12/2002 | Mitchiner et al. ............. 600/9 |

* cited by examiner

*Primary Examiner*—John P. Lacyk
(74) *Attorney, Agent, or Firm*—Knobbe Martens Olson & Bear LLP

(57) ABSTRACT

A magnet keeper-shield assembly adapted to hold and store a permanent magnet used to generate a high gradient magnetic field. Such a field may penetrate into deep targeted tumor sites in order to attract magnetically responsive micro-carriers. The magnet keeper-shield assembly includes a magnetically permeable keeper-shield with a bore dimensioned to hold the magnet. A screw driven actuator is used to push the magnet partially out of the keeper-shield. The actuator is assisted by several springs extending through the base of the keeper-shield.

20 Claims, 10 Drawing Sheets

PERMANENT MAGNET KEEPER-SHIELD ASSEMBLY

CROSS REFERENCE TO RELATED APPLICATION

This application is a continuation of U.S. patent application Ser. No. 09/538,952, filed Mar. 31, 2000, now U.S. Pat. No. 6,488,615 which is incorporated herein by reference in its entirety.

BACKGROUND

Strong magnets include electromagnets and permanent magnets. An electromagnet capable of producing a large magnetic field is cumbersome and requires a very large power supply. Permanent magnets exist of relatively compact size that are capable of producing large magnetic fields. However, permanent magnets cannot be turned off and since their polarity is not rapidly switching, they saturate surrounding permeable material and their emitted field cannot be attenuated. Consequently, permanent magnets are difficult to shield and those that produce large magnetic fields are difficult to handle and store in many settings for which such a magnet might otherwise be useful.

For example, the use of magnetically responsive particles to target drug(s) and/or therapeutic agent(s), device(s) or diagnostic(s) to specific sites through the selective application of a magnetic field, and to achieve prolonged release of high, localized concentrations of drug and/or diagnostic agent by retention of magnetic particles in the region of interest is possible. The externally applied magnetic field produced by a permanent magnet can be used to control the migration and retention of such particles at target sites. However, handling and storage of such a magnet in a clinical setting would be challenging.

SUMMARY

The present invention relates to an apparatus comprising a keeper-shield and a permanent magnet mounted within the keeper-shield. The apparatus renders the magnet easier to store and handle in a variety of settings and for many applications. The details of the invention are set forth in the accompanying drawings and the description below. Other features, objects and advantages of the invention will be apparent from the description and drawings, and from the claims.

DESCRIPTION OF DRAWINGS

The details of one or more embodiments of the invention are set forth in the accompanying drawings and the description below. Other features, objects, and advantages of the invention will be apparent from the description and drawings, and from the claims.

Like reference symbols in the various drawings indicate like elements.

DETAILED DESCRIPTION

Figure 1:
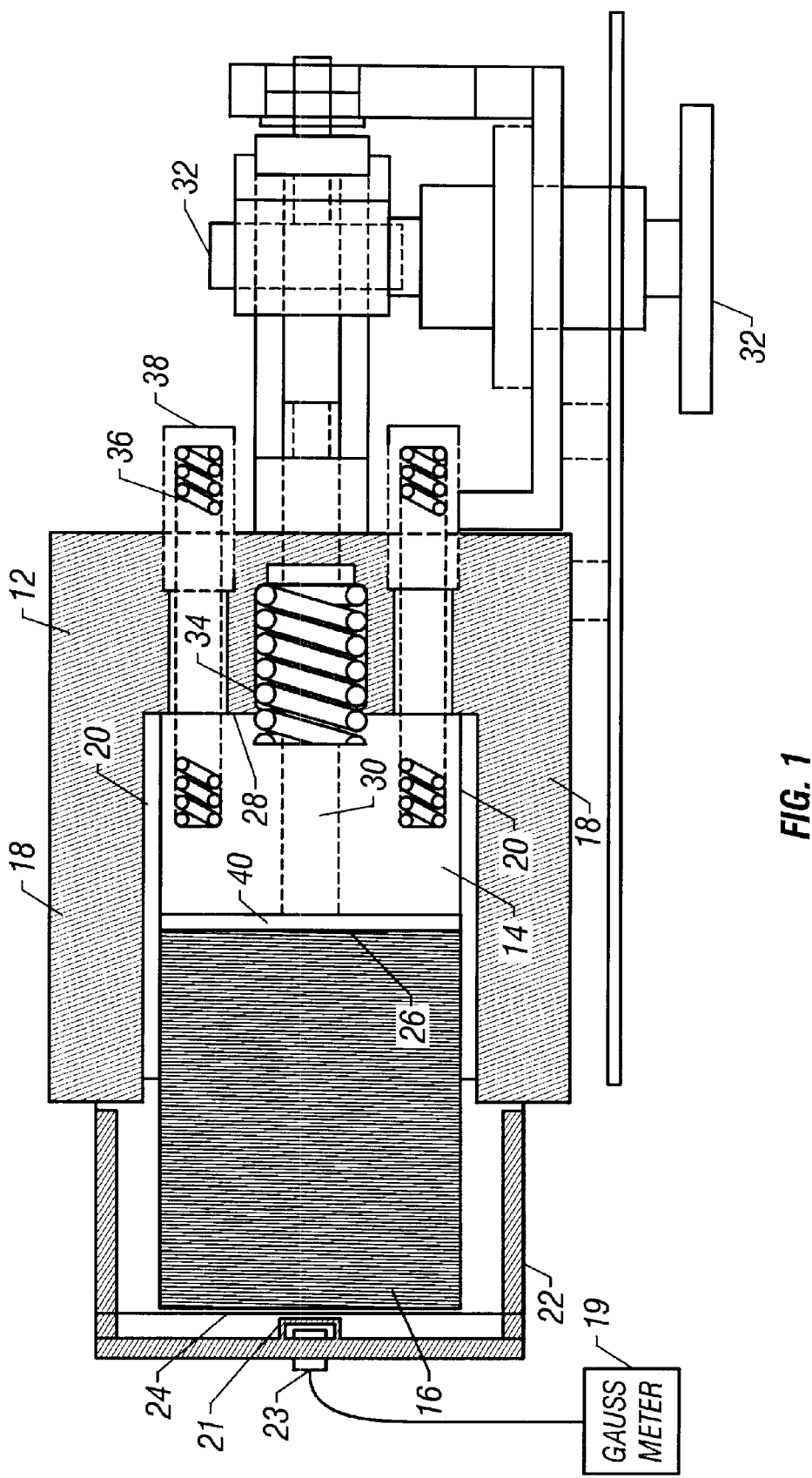
FIG. 1 is a is a sectional view of a keeper-shield assembly in an extended, operating position according to an embodiment.

According to an embodiment of the invention, a magnet keeper-shield assembly is provided to attenuate the magnetic field of a permanent magnet in areas peripheral to one magnetic pole in an extended, operating position and attenuate the entire magnetic field in a retracted, storage position. The magnet keeper-shield assembly is suited to generate and position a high gradient, non-ionizing magnetic field into deep, targeted tumor sites. FIG. 1 illustrates a magnet keeper-shield assembly 10 according to one embodiment. A keeper-shield 12 approximately 10 cm long is provided with a cylindrical bore 14 dimensioned to accept a cylindrical permanent magnet 16. The material used in keeper-shield 12 is substantially permeable to magnetic flux. According to the present embodiment, a soft steel, preferably 1010–1018 steel, is used for keeper-shield 12. Other suitable shielding material includes, for example, mumetal (75%Ni-5%Cu-2%Cr-18%Fe) and supermalloy (79% Ni-15% Fe-5% MO). The keeper-shield material may be laminated. The side wall 18 of keeper-shield 12 has an inner diameter of 5.6 cm and an outer diameter of 8.1 cm. A sleeve 20 of nonmagnetic material is provided along the inner diameter of bore 14 to keep the magnet centered within the bore and prevent surface binding.

A cap 22 may be provided to prevent magnetic objects and debris from magnetically adhering to a front face 24 (north pole) of the magnet. Preferably cap 22 is a Delran cap with an on-axis gaussmeter calibration port 21. The port is a recessed well in the face of the cap positioned over the center axis of front face 24 of magnet 16. The bottom of the port 21 is 10 cm from the front face 24, in the retracted position. The port 21 accepts a probe 23, for example a Hall-effect sensor, of a gaussmeter 19 used to measuring the magnetic field at a calibrated distance from the magnet. A magnetic washer 31 can be embedded in the base of the cap to magnetically adhere the cap the keeper-shield 12.

According to an alternate embodiment, cap 22 is constructed from magnetic material and further increases the volume enclosed with-in the 5 gauss line.

Figure 2:
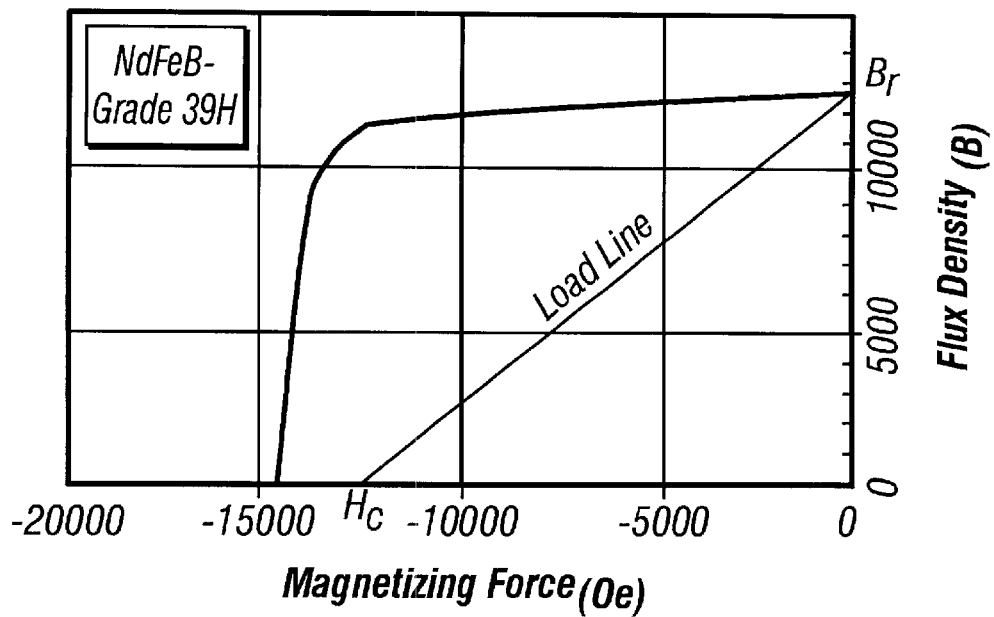
FIG. 2 is a graph showing the de-magnetization curve of the magnet of FIG. 1.

Magnet 16 can be fabricated from any high energy material including alnico, featuring rare earths (atomic number 21, 39, and 57–71) compositions such as samariam-cobalt and neodymium-iron-boron amongst others, ceramics and ceramic oxides such as amongst others ferrite and garnet compositions and permanent magnet superconductor compositions. According to the present embodiment, magnet 16 is fabricated from a composition of neodymium-boron-iron magnet. The magnet is machined to 5.08±0.1 cm dia. by 6.31±0.1 cm length from a powdered metallurgy grade 39H (BHmax at 39MGOe) composition of $Nd_2Fe_{14}B$ that is substantially free of barium and strontium bonding agents. FIG. 2 illustrates the de-magnetization (B-H) curve for grade 39H neodymium-boron-iron composite. Preferably a sealant is applied to the outer surface of magnet 16 to improve corrosion resistance.

Other compositions of NdFeB, and other rare earth, ceramic, or superconducting magnets may be suitable for magnet 16. For example, stronger magnets may be used to produce a stronger field and increased depth of field at the target site. For example, on axis magnetic flux density of magnet 16 (39MGOe), measured with a Lakeshore, Model 410 gaussmeter, is approximately 112 gauss with a magnetic flux density times magnetic gradient product of approximately $3\times10^3$ $gauss^2/cm$ and the flux density of the magnet 16 is approximately 4.5 gauss at 38 cm. The field strength of a magnet of approximately the same dimensions as magnet 16 with a 48 MGOe rating would produce 130 gauss and approximately $4\times10^3$ $gauss^2/cm$ at 10 cm and less than 5 gauss at 38 cm.

Figure 3A:
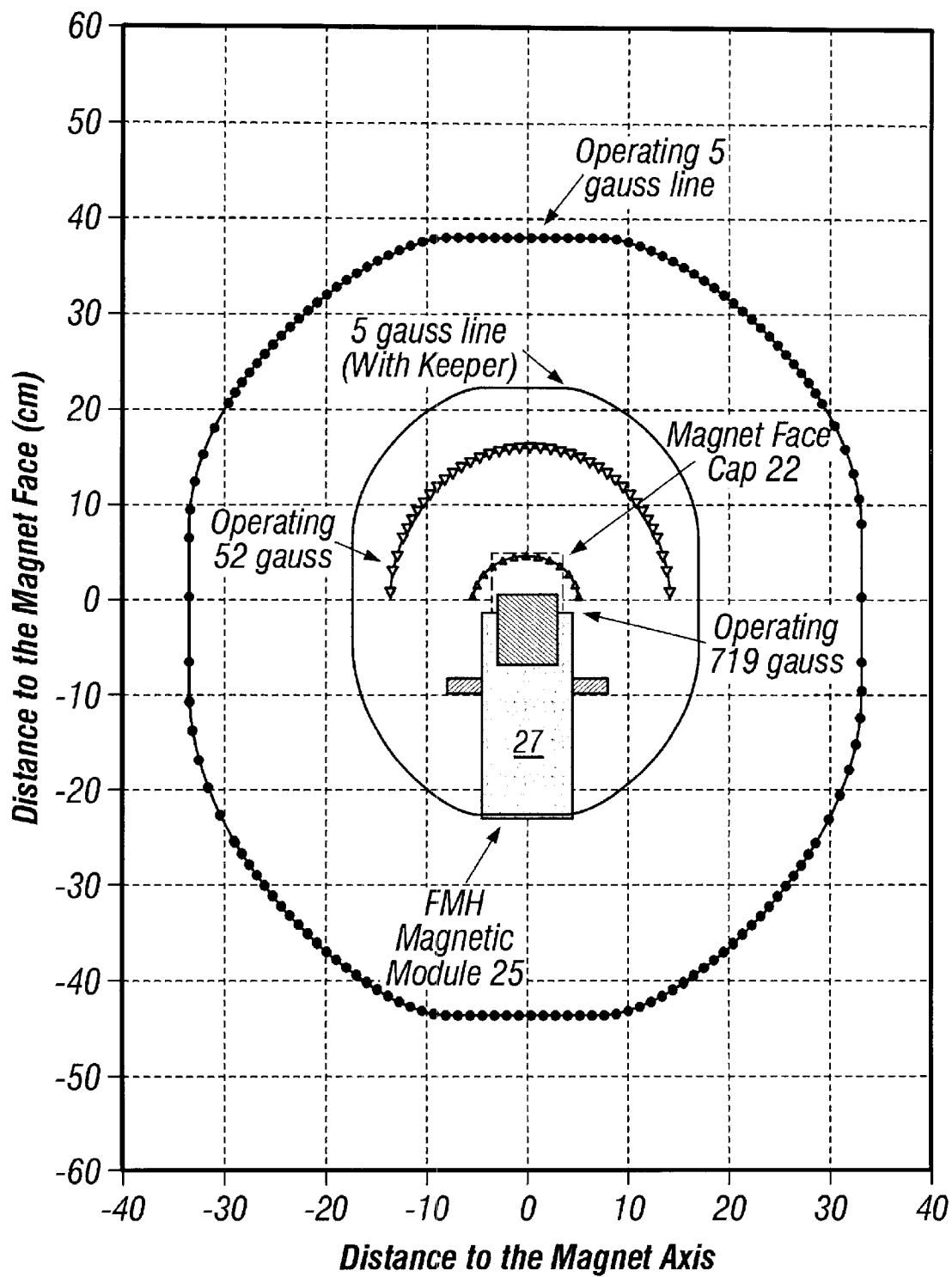
FIGS. 3A and 3B are graphs showing the gradient magnetic field strength of the magnet of FIG. 1.

FIG. 1 illustrates the operating position of the keeper-shield assembly 10 in which magnet 16 extends about 3.5 cm from the front of the keeper-shield 12. FIG. 3A illustrates the magnetic field strength profile around a magnetic module 25 with the magnet 16 in the extended position. The magnetic module 25 includes a dust cover 27 that covers the keeper-shield assembly 10 holding magnet 16. The magnetic field is strongest at front surface 24 and a bottom surface 26, corresponding respectively to the north and south poles of magnet 16.

Front surface 24 may be flat or concave. A concave front face may be provided to focus the magnetic field of the north pole of the magnet.

Figure 3B:
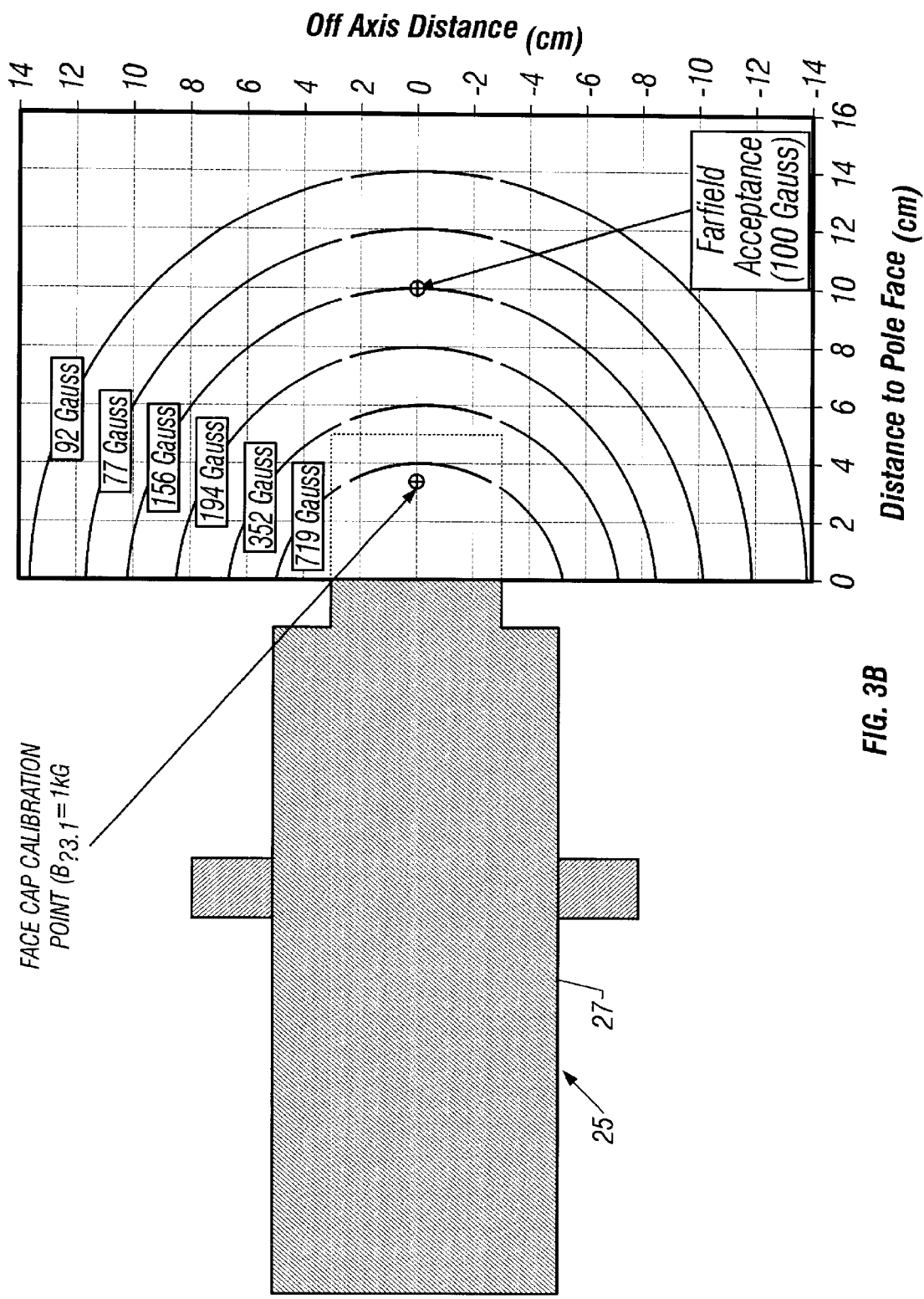

FIG. 3B is a more detailed graph of the magnetic field profile in the operating position. As shown in FIGS. 3A and 3B the magnet produces (on axis) a magnetic flux density of greater than or equal to 50 gauss at 13 cm from the pole face and a magnetic flux density less than or equal to 5 gauss at 38 cm from the pole face 24 in the operating position.

Figure 4:
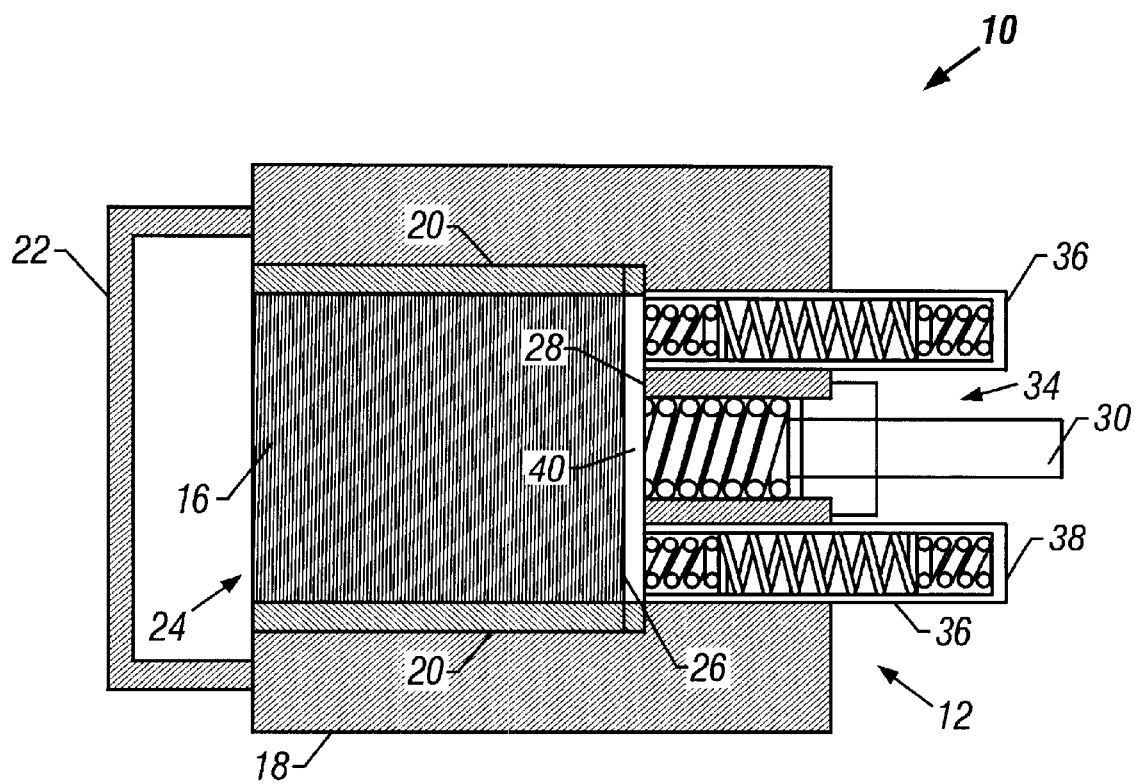
FIG. 4 is a sectional view of the keeper-shield assembly of FIG. 1 in a fully retracted, storage position.

FIG. 4 illustrates the magnet fully retracted in keeper-shield 12 for storage. The magnetically permeable material of the keeper-shield shunts the magnetic field lines, thereby attenuating the magnetic flux around the keeper-shield assembly 10. In the retracted position, the magnet produces 5 gauss at about 22 cm from front face 24. This attenuation of the magnetic flux makes handling and storing the keeper-shield assembly 10 easier, as the attenuation reduces the 5 gauss line to less than 10 cm from the rear of magnetic module 25. Further, the shunting action of the keeper-shield 12 provides long term protection from spurious losses of the field strength. According to the present embodiment, no measurable loss of field strength due to random domain realignment over the life time of the device is expected.

The magnetic field at bottom face 26 (south pole) is comparable to that of front face 24 (north pole). The keeper-shield 12 attenuates the field at the south pole, which reduces radiation interference emission and magnetizable object concerns arising from the tendency of magnetic objects to fly toward the magnet's poles.

The attractive force between bottom face 26 (south pole) and base 28 of the keeper-shield 12 biases the magnet into the fully retracted position (FIG. 4). An actuator rod 30 is provided through the base 28 to push the magnet 16 out of bore 14. According to the present embodiment, actuator rod 30 is driven by a manually powered screw drive mechanism 32. This mechanism could be motor driven.

Due to the strength of the magnet 16, the attractive force between the bottom face 26 and base 28 is very large, and increases at a rate that is approximately proportional to the inverse of the distance between the bottom face 26 and the base 28. The attractive force is greatest in the fully retracted position, at which the attractive force is about 200 pounds.

Figure 5:
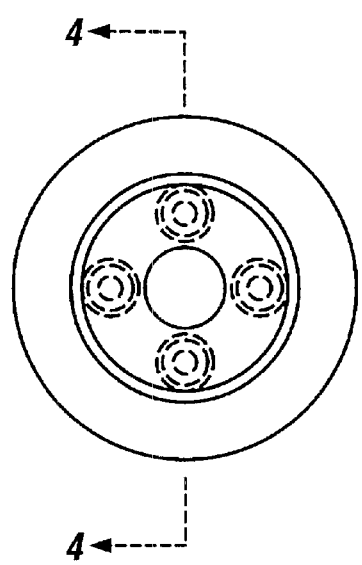
FIG. 5 is a sectional view of the base of the keeper-shield assembly of FIG. 1 showing the position of the springs.

Springs are provided to offset a large portion of this attractive force to ease the action of the actuator rod 30. A relatively strong primary spring 34 is provided in the center of the base around actuator rod 30. Four secondary springs 36 are provided peripherally as shown in FIG. 5. Secondary springs are longer than spring 34 and extend through the base 28 into external spring keeper-shield assemblies 38.

A nonmetallic spacer 40 may be provided on bottom face 26 to prevent the springs from magnetically adhering to the bottom face 26 of the magnet.

Figure 6:
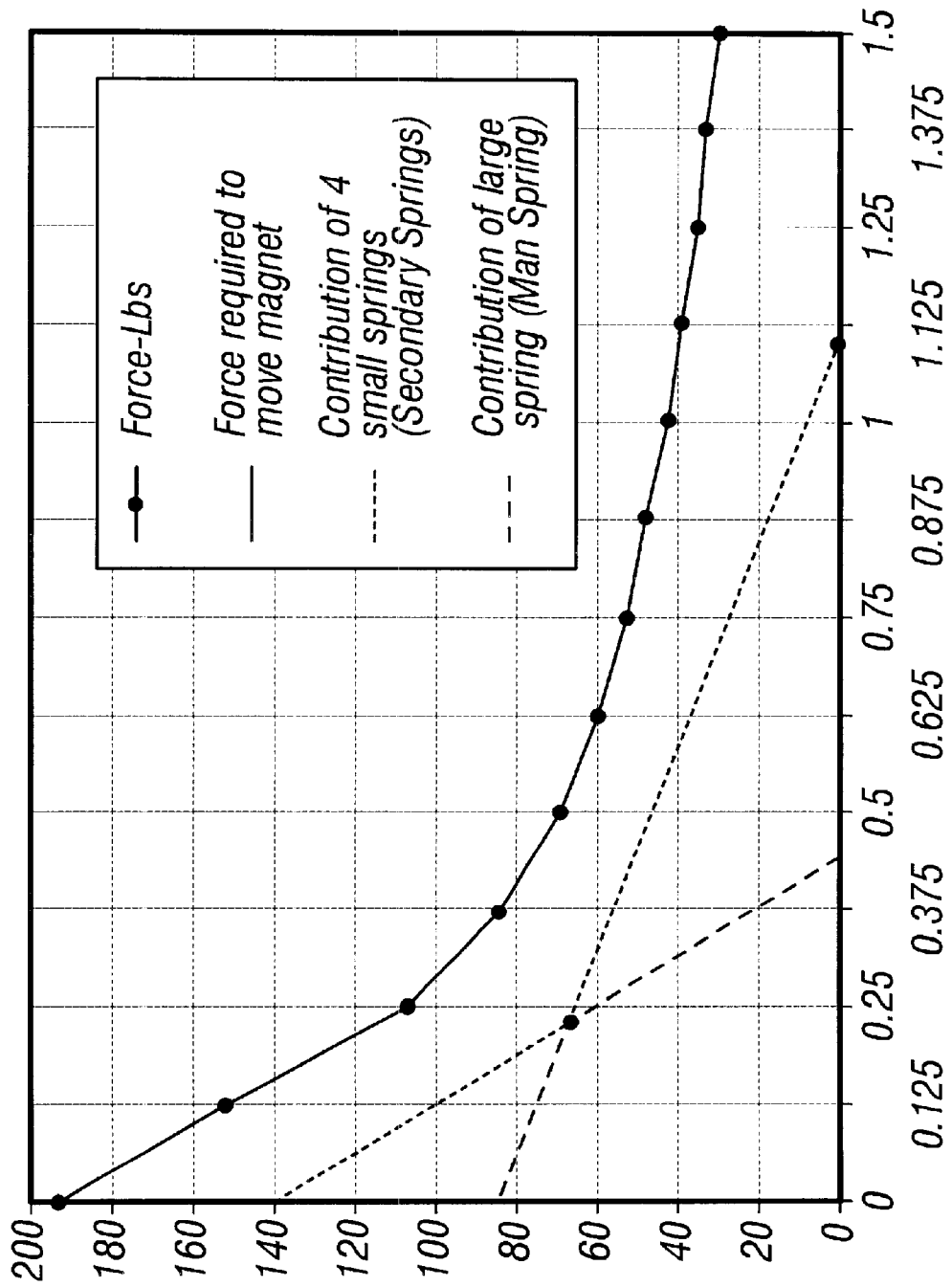
FIG. 6 is a graph showing the force exerted by the springs at different positions of the magnets travel in the keeper-shield assembly of FIG. 1.

The contribution of the springs is cumulative, as shown in FIG. 6. In the fully retracted position, the springs exert a combined force of about 225 pounds on the spacer 40, the primary spring 34 contributing about 140 pounds and secondary springs 36 contributing about 85 pounds. The primary spring 34 contributes the most force up to about 0.25 cm from base 28. After this point the secondary springs 36 contribute the most force.

The springs only contact the spacer for a portion of the magnet's travel through the bore. Primary spring 34 extends about 0.425 cm into the bore 14 when fully extended, and secondary springs 36 extend about 1.2 cm into the bore 14 when fully extended.

Figure 7:
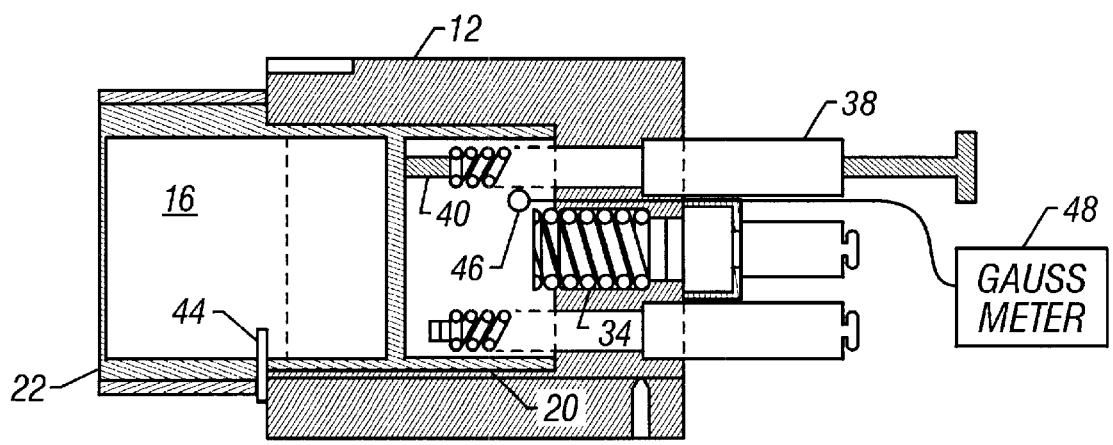
FIG. 7 is a keeper-shield assembly according to another embodiment including a back-up actuator mechanism and magnetic field and magnet position measurement devices.

According to an embodiment shown in FIG. 7, a secondary (back-up) actuator mechanism is provided to extend the magnet in case of failure of the primary actuator mechanism, that is, actuator rod 30 and screw drive mechanism 32. In the event that the primary actuator mechanism fails, a screw that holds a secondary spring in place is removed, and a threaded secondary rod 40 of the same diameter and thread pitch as actuator rod 30 is inserted through the back of keeper-shield 12. Secondary rod 40 is driven by secondary screw drive mechanism to push the magnet 16 out of bore 14.

A sliding position indicator 44 can be attached to the magnet 16 to indicate its position relative to the housing. This allows the user to know the magnet is in the fully extended and fully retracted positions.

A probe 46 for a gaussmeter 48 can be provided at the back of keeper-shield 12. Probe 46 that measures the magnetic field emanated from the back face (south pole) of magnet 16 at that position. As the magnet is extended, the measured field decreases. The measurement is used by a microcontroller 48 to calculate the magnetic field at 1 cm from north pole face 24. This allows the user to select a magnetic field strength desired for a particular application continuously over the range of fields emanated between the fully extended and fully retracted magnet positions.

Figure 8:
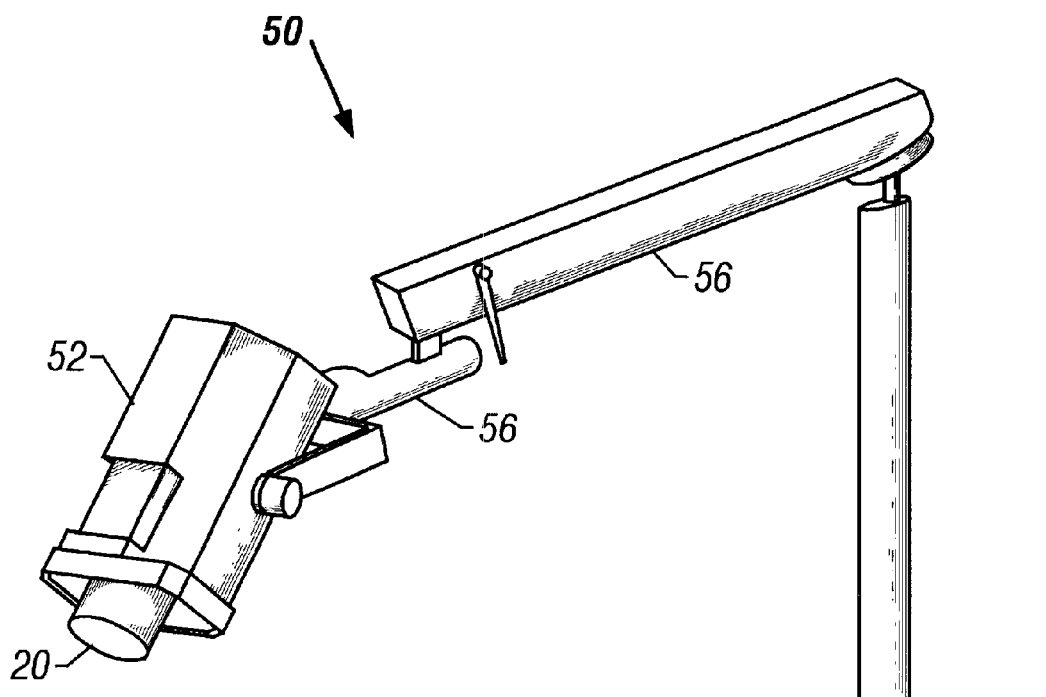
FIG. 8 is a stand according to an embodiment for positioning the keeper-shield assembly.

FIG. 8 illustrates a stand 50 according to an embodiment provided to ease positioning of keeper-shield assembly 10. Keeper-shield assembly 10 is encased in a cover 52 which is attached to a rolling stand 54 by a spring-loaded, counterbalanced articulated arm 56 that can be rotated in three dimensions. The articulated arms 56 and cover 52 may be locked in position to maintain magnet 16 at a desired height and orientation to facilitate precise alignment of the emanated magnetic field onto the targeted site. An articulated magnetic applicator of the type shown in FIG. 8 is manufactured and supplied by FeRx, Incorporated under the name Flexible Magnet Holder (FMH). The FMH houses and positions the magnetic keeper-shield assembly 10.

Keeper-shield assembly 10 with magnet 16 may be used in conjunction with any magnetic particle for any application. Typically, magnetic particles can be designed to deliver any given drug or diagnostic agent. The use of magnetic particles to deliver antitumor agents may useful. The treatment of solid tumors using chemotherapy has been limited by systemic toxicity resulting in sub-optimal dosing, and by multiple other mechanisms (e.g. multiple drug resistance of the tumor cells, tumor architecture limiting access of drug to the tumor cells, volume of distribution for drug) resulting in limited efficacy. Although the magnet can operate to temperatures up to about 140° C., the preferred operating range of the magnet is from about 10° C. to about 50° C. for such clinical applications.

In order to enhance the effectiveness and diminish systemic toxicities of certain chemotherapeutic agents, investigators have attempted to target administration of these drugs by intra-arterial injection immediately proximal to the tumor. One possible reason why an enhancement of the therapeutic index of an agent like doxorubicin is not observed after administration into a tumor-feeding hepatic arteriole is the lack of retention of the agent at the site. Normal clearance mechanisms lead to rapid elimination of the chemotherapeutic from the region of the tumor and, therefore, only transiently increased levels of the drug are regionally available to exert an antitumor effect. Regional therapy achieved through targeted drug delivery using keeper-shield assembly 10 with magnet 16 could improve efficacy by increasing the drug concentration at the tumor while limiting systemic drug concentrations.

Figure 9:
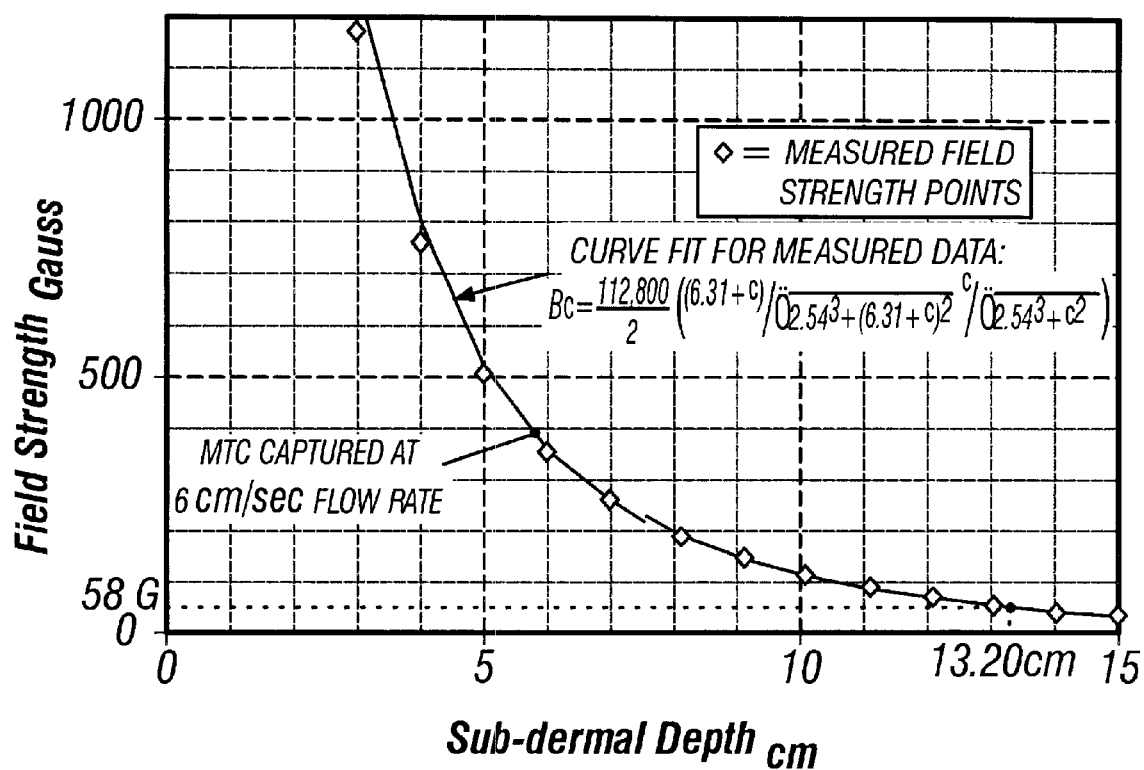
FIG. 9 is a graph showing the field strength as a function of depth in a body.
Figure 10:
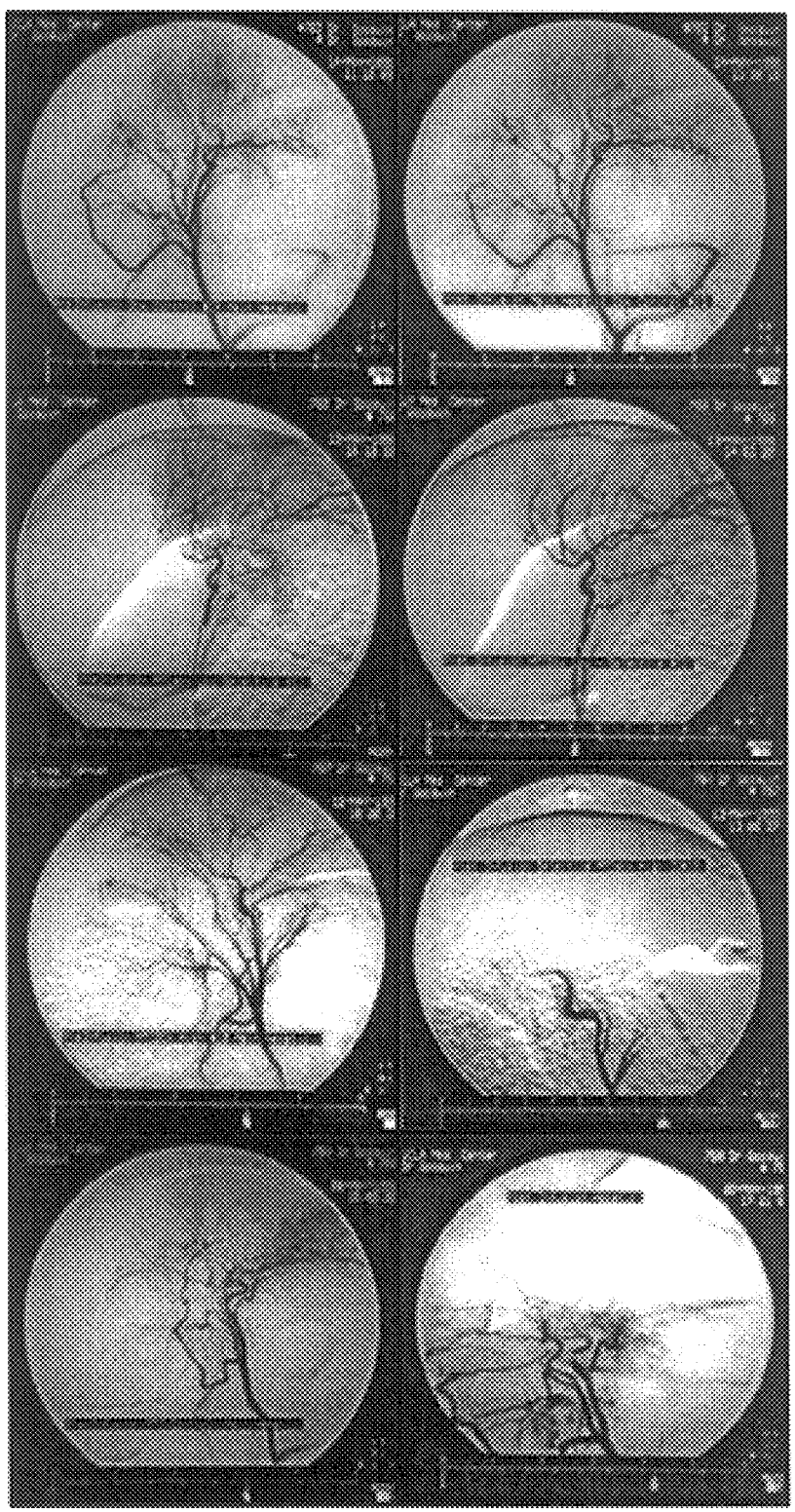
FIG. 10 is pre-(left panels) and post-(right panels) dose angiographies of hepatic arteries for magnetic targeted carriers having various concentrations of doxorubicin adsorbed thereon (MTC-DOX).
Figure 11:
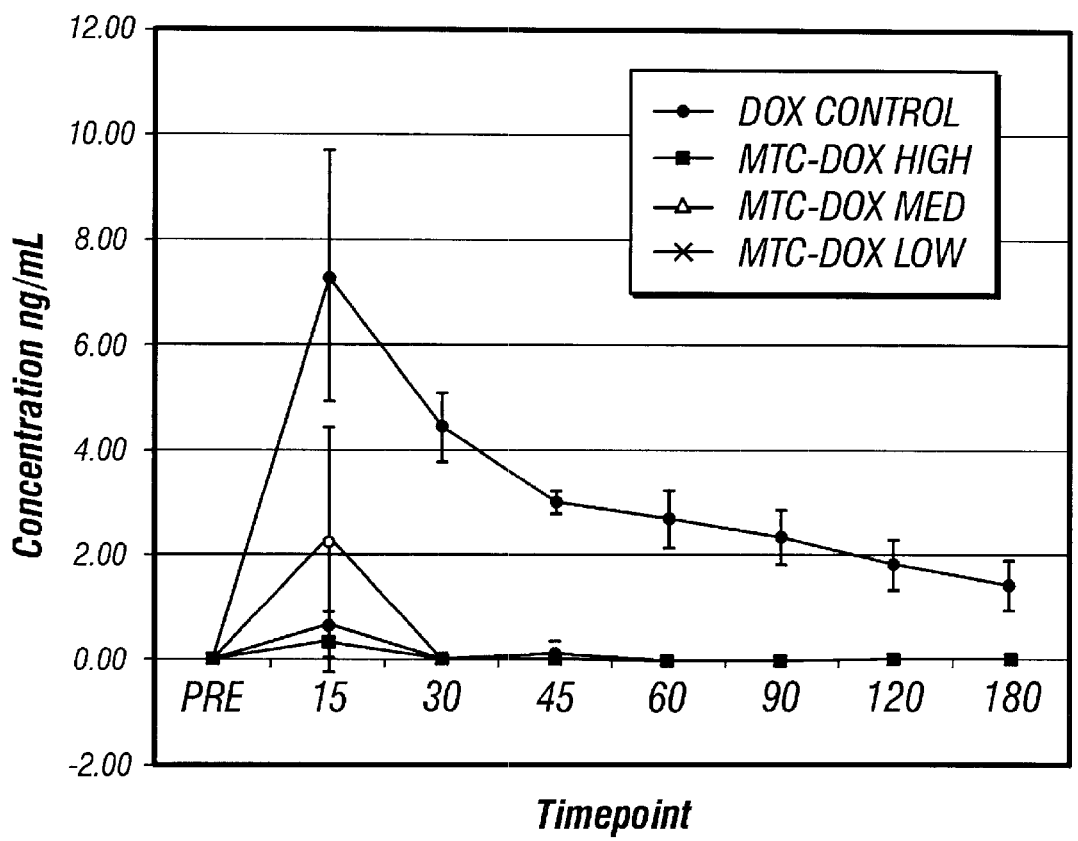
FIG. 11 is toxicokinetic data for patients undergoing injection of magnetic particles having doxorubicin attached thereon and targeted to a desired location in the patient's body through selective application of a magnetic field.

The keeper-shield assembly 10 is positioned over a target site on the patient. The magnet is extended from the fully retracted position (FIG. 4) to the operating position (FIG. 1) by manipulating screw drive mechanism 32. The keeper-shield assembly 10 and patient are maintained in this position for a prescribed time period that may be from several seconds to many hours. After sufficient exposure, the magnet is retracted to the fully retracted position for storage. FIG. 9 shows the field strength (on axis) of the magnet 16 as a function of depth.

EXAMPLE 1

Magnetic targeted carriers (MTCs) are a proprietary microsphere composite of elemental iron and activated carbon. See for example, U.S. Pat. Nos. 5,549,915, 5,651,989, 5,705,195, and co-pending U.S. Ser. Nos. 09/003,286 and 09/226,818. MTCs combine elemental iron and activated carbon in microspheres of 0.5–5 $\mu$m. The activated carbon is capable of adsorbing and desorbing a wide variety of drug substances. The elemental iron component of the microspheres allows targeting and local retention after hepatic arterial administration, by placement of an external magnet on the body surface. MTC-doxorubicin (MTC-DOX) can thus be administered by selective catheterization of one of the hepatic arterioles feeding an HCC. Placement of the external magnet over the region of the tumor allows for efficient targeting of the MTC-DOX. MTC-DOX (doxorubicin) is designed for the magnetically targeted site-specific delivery to a liver tumor in the presence of an externally applied magnetic field.

Eighteen swine were assigned to 6-treatment groups including 3 control groups and 3 doses of the MTC-DOX preparation. Animals were given a single administration of test article and evaluated over 28 days and then sacrificed. There were no adverse effects in the DOX alone group. Biologically significant treatment-related gross and microscopic lesions were limited to the targeted area only of the liver in groups receiving $\geq 75$ mg of MTC, and the "no adverse effect level" NOAEL was determined to be 25 mg MTC/2 mg DOX. Evidence for a possible synergistic effect between MTC and DOX was observed, where parenchyma regenerating from the damage caused by targeted MTCs caused the dividing hepatocytes to be more sensitive to DOX.

Materials

The designation of the test article used was MTC-doxorubicin (MTC-DOX). Doxorubicin-HCl Injection, USP was purchased from Fujisawa USA. The drug carrier was MTC and manufactured by FeRx Incorporated. The MTCs were rendered sterile by gamma irradiation. The vehicle for injection is 10% mannitol and 0.5% carboxymethylcellulose in WFI. The designation of the magnet assembly is Flexible Magnet Holder (FMH) and is manufactured and supplied by FeRx Incorporated. The drug substance (doxorubicin) and vehicle were supplied as sterile solutions, and the drug carrier was supplied as a sterile dry powder. The magnet (1.97 in (w)×2.5 in (l)) housed in the FMH is a rare-earth NdFeB permanent magnet (5 kgauss at the pole face) purchased from Magnet Sales, Inc. of Culver City, Calif.

For administration, a vial containing 100 mg of MTC drug carrier product was incubated at room temperature (18 to 25° C.) with 8 mg (4 mL) of doxorubicin (2 mg/mL) for 30 minutes. The MTC-doxorubicin solution was then diluted with 16 mL of vehicle for injection and sonicated for 30 seconds using a Cole-Palmer Ultrasonic Cleaner using the "Sonic Degas" setting prior to administration. The resulting dose solution had a concentration of 0.4 mg/ml of doxorubicin and 5.0 mg/ml of MTC drug carrier.

Yorkshire domestic swine used in this study were obtained from S & S Farms (San Diego, Calif.). The animals were laboratory bred and were experimentally naive at the outset of the study. Animals selected for use in this study were as uniform in age and weight as possible. They were generally prepubertal to young adult animals approximately 3 to 4 months of age, and their body weights ranged from 23 to 29 kg. All animals were acclimated to laboratory conditions for a minimum of 7 days prior to study initiation.

Methods

General Description—A total of eighteen animals were randomly assigned to six treatment groups of three animals/group as shown in Table 1 below. Each animal received a single dose of test article by hepatic intra-arterial infusion. The animals were evaluated for changes in clinical signs, body weight, clinical pathology indices, and other parameters as described below. All animals were euthanized on Day 29, except for those animals that required early sacrifice. A full necropsy was conducted on all animals that survived to the end of the study, and a partial necropsy was conducted on those animals that were sacrificed early. A full panel of tissues was collected for histopathological evaluation.

Group Assignments and Dose Levels—Animals were dosed using a fixed concentration of the test article. The low, medium, and high MTC-DOX doses varied as a function of the infusion volume. Table 1 lists the total dose and the mg/kg dose based on the dose calculated from the average pig weight determined for the respective groups.

TABLE 1

Group assignments and dose levels

| Group No. | Animals/ Group | Treatment Group | Dose (mg/kg)[1] Dox | Dose (mg/kg)[1] MTC | Total Dose (mg) Dox | Total Dose (mg) MTC | Volume |
|---|---|---|---|---|---|---|---|
| 1 | 3 | Vehicle Control | 0.00 ± 0.00 | 0.00 ± 0.00 | 0 | 0 | 45 mL |
| 2 | 3 | Dox-High Control | 0.73 ± 0.04 | 0.00 ± 0.00 | 18 | 0 | 45 mL[2] |
| 3 | 3 | MTC-High Control | 0.00 ± 0.00 | 8.85 ± 0.83 | 0 | 225 | 45 mL[3] |
| 4 | 3 | MTC-Dox-Low | 0.08 ± 0.00 | 1.01 ± 0.03 | 2 | 25 | 5 mL[4] |
| 5 | 3 | MTC-Dox-Med | 0.22 ± 0.01 | 2.79 ± 0.16 | 6 | 75 | 15 mL[4] |
| 6 | 3 | MTC-Dox-High | 0.72 ± 0.06 | 8.94 ± 0.71 | 18 | 225 | 45 mL[4] |

[1]The dose in mg/kg was estimated based on the average pig weight for each treatment group.
[2]The dose solution had a concentration of 0.4 mg/ml of doxorubicin.
[3]The dose solution had a concentration of 5.0 mg/ml of MTC drug carrier.
[4]The dose solution had a concentration of 0.4 mg/ml of doxorubicin and 5.0 mg/ml of MTC drug earner.

Catheterization procedure—The animals were fasted overnight (approximately 12–15 hours) prior to surgery. In preparation for the procedure, each animal was weighed and pre-anesthetized with 150-mg ketamine and 150 mg xylazine. The right hind leg of each animal was disinfected with betadine solution and the surgical site was covered with a Steridrape. All study personnel wore surgical gloves, gown or scrubs during the catheterization and administration procedure. Under general anesthesia, a skin incision was made in the right inguinal area and the animals were cannulated via the femoral artery using standard percutaneous techniques. Animals were administered 5000 IU of heparin (Elkins-Sinn) systemically prior to delivery as prophylaxis against catheter induced thrombosis.

Under fluoroscopy, a 5-french angled glide catheter (Cook, Inc., Bloomington, Ind.) and a 0.035 inch angled glidewire (Meditech Inc., Watertown, Mass.) were inserted into the celiac artery. The common or proper hepatic artery was catheterized, and angiography was performed to select a segmental branch of the hepatic artery that provided adequate accessibility to the desired lobe of the liver to which the test article was targeted. The right, middle, or left hepatic artery, or segmental branch thereof, was then catheterized with a Tracker 325 catheter (Target, Inc., Freemont, Calif.) and Taper 22 wire (Target Inc., Freemont, Calif.). Angiography was then performed to verify catheter placement in the desired segmental branch of the hepatic artery feeding the selected lobe of the liver.

Magnet Placement and Depth Measurements—Using angiography, placement of the magnet was determined by placing a 2-inch diameter metal disk on the ventral surface of the pig positioned central to the capillary blush, and approximately 1–2 cm distal to the catheter tip. The disk's position was verified under angiography, and the disk was outlined on the skin surface to guide placement of the magnet. Once the magnet position was determined, a depth from the catheter tip to the center point of the magnet was determined by angiography. For groups 1 and 2, a depth measurement was done by placing a metal ruler on the ventral surface of the skin, distal to the catheter position, and measured by angiography. Following the angiography procedures, the north pole of the 5 kgauss rare-earth magnet housed in the flexible magnet keeper-shield assembly was centered in the marked position on the surface of the animal. The magnet was kept in position during the entire infusion procedure (groups 3, 4, 5, 6) and for an additional 15 minutes following the completion of the infusion.

Test Material Infusion—The test article dose volume was infused as repeated cycles of 7.5 mL infusions at an infusion rate of 2 mL/min (Group 4 (MTC-DOX low dose group) received a single 5-mL injection), as described in Table 2. The cycles were repeated every 15 minutes until all of the dose volume was administered. Prior to each infusion cycle, the test article suspension was kept uniform by passing the material between two connected syringes 5 times.

TABLE 2

Test material infusion parameters

| Group No. | Treatment Group | Dose Volume | MTC (mg) per Infusion Cycle | Dox (mg) per Infusion Cycle | Volume (mL) per Infusion Cycle | Number of Infusion Cycles |
|---|---|---|---|---|---|---|
| 1 | Vehicle High Control | 45 | 0 | 0 | 7.5 | 6 |
| 2 | Dox-High Control | 45 | 0 | 3 | 7.5 | 6 |
| 3 | MTC-High Control | 45 | 37.5 | 0 | 7.5 | 6 |
| 4 | MTC-DOX-Low | 5 | 25.0 | 2 | 5.0 | 1 |
| 5 | MTC-DOX-Med | 15 | 37.5 | 3 | 7.5 | 2 |
| 6 | MTC-DOX-High | 45 | 37.5 | 3 | 7.5 | 6 |

Post Infusion Angiography—At the end of the infusion, an angiogram was done to verify the patency of the arteries in the selected lobe of the liver. Angiography was performed through the Tracker 325 catheter. The Tracker 325 was then removed and repeat angiography of the common or proper hepatic artery was performed through the 5-french glide catheter to determine the patency of the hepatic arterioles.

Toxicokinetic Analysis—Aliquots of approximately 2.0 mL of whole blood were collected in EDTA-containing tubes from all animals in Groups 2, 4, 5 and 6 on Day 0 prior to dosing, and at 15, 30, 45, 60, 90, 120 and 180 minutes post dose. The samples were mixed immediately by inverting at least six times, and then centrifuged. Analysis of plasma doxorubicin levels were quantitated by HPLC.

Results

Angiography—Table 3 provides information on the location of the target region within the liver, including depth relative to catheter position, and degree of embolization as observed by angiography.

TABLE 3

Post-treatment analysis of embolization

| Group No. | Treatment Group | Animal No. | Liver Segments Targeted | Depth (cm) | Emboliza- tion[2] |
|---|---|---|---|---|---|
| 1 | Vehicle | 754 | 2,3,4 | 9.5 | − |
|   | Control | 755 | 2,3,4 | 8.6 | − |
|   |   | 766 | 2,3,4,8 | 7.1 | NA[3] |
|   |   |   |   | Mean 8.4 |   |
|   |   |   |   | SD 0.99 |   |
| 2 | Dox | 751 | 2,3,4,8 | 9.1 | + |
|   | Control | 763 | 2,3,4 | 8.4 | − |
|   |   | 764 | 7,8 | 8.3 | − |
|   |   |   |   | Mean 8.6 |   |
|   |   |   |   | SD 0.36 |   |
| 3 | MTC | 750 | 2,3,4,8 | 9 | + |
|   | Control | 753 | 4,7,8 | 10.8 | ++ |
|   |   | 761 | 4,8 | 10.9 | +++ |
|   |   |   |   | Mean 10.2 |   |
|   |   |   |   | SD 0.87 |   |
| 4 | MTC-DOX | 749 | 2,3,4,8 | 8.5 | − |
|   | Low | 752 | 2,3,4,8 | 8.8 | − |
|   |   | 760 | 2,3,4,8 | 7.8 | − |
|   |   |   |   | Mean 8.4 |   |
|   |   |   |   | SD 0.42 |   |
| 5 | MTC-DOX | 723 | 2,3,4,8 | 9.5 | + |
|   | Medium | 756 | 4,7,8 | 11.5 | +/− |
|   |   | 762 | 2,3,4,7,8 | 8 | − |
|   |   |   |   | Mean 9.7 |   |
|   |   |   |   | SD 1.43 |   |
| 6 | MTC-DOX | 748 | 2,3,4,5,8 | 8 | +++ |
|   | High | 757 | 2,3,4,8 | 11.7 | +++ |
|   |   | 765 | 4,7,8 | 10 | +++ |
|   |   |   |   | Mean 9.9 |   |
|   |   |   |   | SD 1.51 |   |

NA = not available
[2]Symbol Definition:
(−) No observed embolization
(+) Minor embolization of selective arterioles
(++) Moderate embolization of selective arterioles
(+++) Significant to complete embolization of selective and main arterioles
[3]End procedure angiography was not done. The animal woke up following the procedure and the catheter had dislodged from the original position.

Toxicokinetic Data—Plasma concentrations of doxorubicin were analyzed by HPLC. Samples were taken from Groups 3, 4, 5, and 6 prior to dosing and at 15, 30, 45, 60, 90, 120, and 180 minutes post-dose. Results show that the MTC-DOX groups as compared to the doxorubicin control group have little or no circulating doxorubicin as shown in FIG. 1. These results suggest that the drug remained localized primarily to the targeted site in the MTC-DOX treatment groups.

Microscopic Pathology, Targeted Liver—Direct treatment related microscopic changes were primarily limited to the targeted region of the liver in those groups receiving MTC particles. In general, microscopic changes increased in severity in proportion to the increasing dose of MTC particles, with the most severe liver changes in both groups receiving the high dose of MTC particles (Groups 3 and 6).

As a result of the use of the permanent magnet, extravasation of MTC particles into the portal area tissue (including the walls of the hepatic artery branches) was noted in all animals receiving MTC particles. MTC particles in the Kupffer cells of the hepatic lobule was noted in all groups receiving MTC, although only in one of the three animals (at a minimum severity) in the group receiving the MTC-DOX low dose (group 4). In most animals, multinucleated giant cells were associated with the presence of MTC particles in the portal area tissue.

Several other treatment related changes were present affecting the portal regions of the targeted liver and were present in a dose-related fashion. Portal fibrosis (bridging), a change characterized by bands of fibrous connective tissue connecting adjacent portal areas, was a prominent change except in the MTC-DOX low dose group. Bile duct hyperplasia consistently accompanied the bridging fibrosis.

Bile pigment, peribiliary fibrosis, neutrophilic inflammation of bile ducts and bile duct rupture were variably present in the groups receiving 75 mg of MTC particles or greater (Groups 3, 5, and 6). Chronic/active inflammation was only seen in those animals receiving the high dose of MTC particles (Groups 3 and 6). Of these changes, only mild focal peribiliary fibrosis was present in a single animal receiving the MTC-DOX low dose.

In the targeted liver, severe necrosis of entire hepatic lobules was present in the MTC-DOX high dose group. The MTC control group had moderate necrosis of the targeted region and only one animal in the MTC-DOX Medium dose group had mild necrosis of the hepatic lobules in the targeted liver. Areas of chronic/active inflammation surrounded the areas of necrosis in the MTC-DOX High dose group only. This inflammatory reaction was a response by the body to surround and isolate the zones of necrosis.

Microscopic Pathology, Non-Targeted Liver—In the groups receiving the high dose of MTC particles (Groups 3 and 6), a mild to moderate presence of MTC particles were seen in the hepatic artery, portal areas and hepatic lobules (Kupffer cells) in the non-targeted regions of the liver. The presence of these particles in the non-targeted region of the liver did not appear to cause any associated damage to the liver. Moderate bile-stasis in the non-targeted region of the liver was present in only one animal receiving the MTC-DOX high dose and was considered to be secondary to the severe changes occurring in the targeted region of the liver in that animal. No other groups had particles outside of the targeted region.

Microscopic Pathology, Other Tissues—MTC particles were present within submucosal arteries in the stomach of a single animal in the MTC-DOX High dose group. These particles were associated with a minimal accumulation of multinucleated giant cells but otherwise, there were no related changes in the stomach.

Changes Indirectly Related to Treatment—Microscopic changes indirectly related to treatment were found in the MTC-DOX High dose group only. These changes were present in the lung, heart, and spleen. These changes were inflammatory in nature and likely developed secondary to the clinical deterioration of the animals resulting from the hepatic pathology.

In the lung of two of the three animals from group 6, there was severe lung inflammation with bacteria in the bronchi. These changes were characteristic of a bacterial bronchopneumonia developing either as an acquired infection or via aspiration. In one animal, pleural fibrosis and pleura inflammation was associated with the pneumonia. Neutrophilic inflammation of the pericardium in one of the animals from this group was also most likely due to bacterial infection. Granulomatous inflammation or neutrophilic inflammation in the spleen of 2/3 animals from this group were likely extensions of inflammation in other tissues of the body.

Conclusions

Eighteen female domestic swine were administered a pulsatile administration of one of the following treatments via the hepatic artery: vehicle control (negative control), 18 mg doxorubicin, 225 mg MTC, 25 mg MTC/2 mg doxorubicin, 75 mg MTC/6 mg doxorubicin, or 225 mg MTC/18 mg doxorubicin. Toxicokinetic results indicate that doxorubicin is not freely circulating in any of the MTC-DOX groups, and therefore suggests that the drug has been localized to the targeted site through the use of the externally placed permanent magnet. Based upon the gross and the microscopic pathology, the NOAEL was 25 mg MTC/2 mg doxorubicin.

EXAMPLE 2

Clinical Engineering at the UCLA Medical Center has evaluated the FeRx Flexible Magnet Holder lot number D002.

A three-part test was performed to determine its potential effect on the equipment that will be present in angiographic procedure room. The field strength of the magnet holder was set at 1,000 gauss.

1. Fluroscopic X-Ray Unit

This test was made to determine the influence of the magnet to the image intensifier in various distances. A line pair resolution phantom was mounted to the center of the image intensifier and successive readings were made. All distance measurements are referenced to the central beam of the 1.1. For the type of procedure to be performed, an evaluation was made using the 9-inch and 12-inch field modes. In both cases the magnet started to influence the TV image at a 36-inch distance. At 12-inch, the image resolution dropped off completely.

2. Infusion Devices

Various infusion devices were tested within close proximity to the Flexible Magnet Holder. The Baxter model 6201, 6301, and PCAII were the only devices affected by the Flexible Magnet Holder. When the Magnetic Module was within one inch of these units it caused a "Door Open" alarm, stopping infusion.

3. Physiological Monitoring System

The Marquette physiological monitoring system, model Tramscope 12C, was tested within close proximity (up to one inch) to the device without any interference with monitoring performance.

Caution should be used when this device is in close proximity to the above equipment. When not in use, this device should be at least 36 inches from the X-Ray image intensifier. It is not to be used in presence of any implantable devices or respiratory ventilators.

Note that since the maximum field strength of the magnet was measured to be 1,073 gauss, to increase the above mentioned "safe" distances by 10% would be more than sufficient.

It is Clinical Engineering's recommendation that the Flexible Magnet Holder is safe to be utilized with human subjects who are not on life support and/or saving devices, based on the specified criteria in the patient inclusion selection of the Protocol #MTC-DOX001 (attached).

A number of embodiments of the invention have been described. Nevertheless, it will be understood that various modifications may be made without departing from the spirit and scope of the invention. Accordingly, other embodiments are within the scope of the following claims.

What is claimed is:

1. A magnet keeper-shield assembly for housing a magnet, said magnet keeper-shield assembly comprising:
   a keeper-shield comprising a material substantially permeable to a magnetic flux;
   a cavity in the keeper-shield, said cavity comprising an inner side wall and a base, and said cavity being adapted to accept a magnet having a front and a bottom face;
   an actuator extending through the base;
   a plurality of springs extending through the base, said springs operative to exert a force in a range from about 175 pounds to about 225 pounds on the bottom face of the magnet in a retracted position, and
   wherein said magnet produces at least about 118 gauss at a distance of about 10 cm from the front face in the extended position and produces at most about 5 gauss at a distance less than or equal to about 22 cm from the front face in the retracted position.

2. The magnetic keeper-shield assembly of claim 1, wherein the actuator is adapted to extend in the keeper-shield and push the magnet out of the keeper-shield.

3. The magnetic keeper-shield assembly of claim 1, wherein the bottom face includes a spacer comprising a nonmagnetic material, and the actuator contacts the spacer.

4. The magnetic keeper-shield assembly of claim 1, where in said magnet comprises material selected from the group consisting of rare earth elements, ceramics, ceramic oxides, ferrites, and garnets.

5. The magnetic keeper-shield assembly of claim 1, wherein the magnet comprises material selected from the group consisting of NdFeB, AlNiCo, and SmCo.

6. The magnetic keeper-shield assembly of claim 1, wherein the keeper-shield comprises a material permeable to a magnetic flux.

7. The magnetic keeper-shield assembly of claim 1, further comprising a cap magnetically adhered to the keeper-shield over the front face of the magnet, wherein said cap comprises a port.

8. The magnetic keeper-shield assembly of claim 1, further comprising a screw drive mechanism operatively connected to the actuator.

9. The magnetic keeper-shield assembly of claim 1, further comprising a plurality of bores in the keeper-shield, each bore adapted to accept a particular one of said springs, and wherein at least one of said bores is adapted to accept a second actuator rod.

10. The magnetic keeper-shield assembly of claim 1, further comprising a sleeve situated between said inner wall and said magnet.

11. The magnetic keeper-shield assembly of claim 1, further comprising a position indicator.

12. A method of in vivo delivery of magnetic particles, the method comprising:
   administering a composition into a patient, said composition comprising magnetic particles;
   extending a magnet having a front and a bottom face from a shielding keeper-shield to produce at least about 118 gauss at a distance of about 10 cm from the front face;
   positioning said magnet over a desired location on the patient; and
   directing said particles to a desired location in the patient with the use of a magnetic field provided by said magnet.

13. The method of claim 12, further comprising retracting said magnet into the keeper-shield after said use of magnetic field, to produce at most about 5 gauss at a distance less than or equal to about 22 cm from the front face.

14. A method for decreasing systemic toxicity of a drug comprising:
   preparing a composition comprising magnetic particles in combination with said drug;
   administering said composition into a patient;
   extending a magnet having a front and bottom face from a keeper-shield to produce at least about 118 gauss at a distance of about 10 cm from the front face;
   positioning said magnet over a desired location on the patient; and
   directing said magnet particles to the desired location in the patient with the use of a magnetic field provided by said magnet.

15. The method of claim 14, further comprising retracting said magnet into the keeper-shield after said use of magnetic field, to produce at most about 5 gauss at a distance less than or equal to about 22 cm from the front face.

16. A method for decreasing systemic circulation of agents selected from the group consisting of diagnostic, therapeutic, and combinations thereof, comprising:
   preparing a composition comprising magnetic particles in combination with said agent;
   administering the composition into a patient, said composition comprising magnetic particles having the agent attached thereon;
   positioning a permanent magnet over a desired location on the patient; and
   directing said magnetic particles to the desired location in the patient with the use of a magnetic field provided by said magnet.

17. The method of claim 16, further comprising retracting said magnet into the keeper-shield after said use of magnetic field, to produce at most about 5 gauss at a distance less than or equal to about 22 cm from the front face.

18. The method of any of claims 12, 14 and 16, wherein said magnetic particles comprise carbon and iron.

19. The method of any of claims 12, 14 and 16, wherein said desired location is a tumor.

20. A method for providing variable field strength from a permanent magnet comprising extending the magnet from a keeper-shield assembly, wherein the keeper-shield assembly comprises:
   a keeper-shield comprising a material substantially permeable to magnetic flux;
   a cavity in the keeper-shield, said cavity comprising an inner side wall and a base, and said cavity being adapted to accept a magnet having a front and a bottom face;
   an actuator extending through the base;
   a plurality of springs extending through the base, said springs operative to exert a force in a range from about 175 pounds to about 225 pounds on the bottom face of the magnet in a retracted position; and
   wherein said magnet produces at least about 118 gauss at a distance of about 10 cm from the front face in the extended position and produces at most about 5 gauss at a distance less than or equal to about 22 cm from the front face in the retracted position.

* * * * *